United States Patent [19]
Agnus et al.

[11] Patent Number: 6,086,916
[45] Date of Patent: Jul. 11, 2000

[54] PROGESTERONE TABLET AND ITS MANUFACTURING PROCESS

[75] Inventors: Benoît Agnus, Bry sur Marne; Antoine Besins, Paris, both of France

[73] Assignee: Laboratoires Besins Iscovesco, France

[21] Appl. No.: 09/268,351

[22] Filed: Mar. 16, 1999

Related U.S. Application Data

[63] Continuation of application No. PCT/FR98/02790, Dec. 18, 1998.

[30] Foreign Application Priority Data

Dec. 19, 1997 [FR] France .................................. 97 16168

[51] Int. Cl.[7] ....................................................... A61K 9/20
[52] U.S. Cl. ............................ 424/464; 424/465; 424/470
[58] Field of Search ..................................... 424/464, 465, 424/470

[56] References Cited

U.S. PATENT DOCUMENTS

| | | | |
|---|---|---|---|
| 4,115,563 | 9/1978 | John | 424/241 |
| 4,196,188 | 4/1980 | Besins | 424/37 |
| 4,911,921 | 3/1990 | Denton et al. | 424/80 |
| 5,620,705 | 4/1997 | Dong et al. | 424/472 |

FOREIGN PATENT DOCUMENTS

| | | |
|---|---|---|
| 0 330 284 | 8/1989 | European Pat. Off. . |
| 0 335 970 | 9/1992 | European Pat. Off. . |
| 2 383 664 | 10/1978 | France . |
| 2 408 345 | 6/1979 | France . |
| 95/05807 | 3/1995 | WIPO . |

*Primary Examiner*—James M. Spear
*Attorney, Agent, or Firm*—Larson & Taylor PLC

[57] ABSTRACT

The invention concerns a progesterone tablet characterised by the fact that its excipient content is at most 45%, preferably at most 40%, and yet more preferably at most 38%, the percentages being expressed in weight relative to the total dry matter of the tablet.

11 Claims, 2 Drawing Sheets

PROGESTERONE TABLET AND ITS MANUFACTURING PROCESS

This application is a continuation of PCT/FR98/02790 filed Dec. 18, 1998.

The present invention concerns a progesterone tablet as well as a process for its manufacture.

FIELD OF THE INVENTION

Natural progesterone is a hormone which, in women, is synthesized mainly by the ovary and, to a lesser degree, by the adrenal glands and the placenta during the second part of pregnancy. Non endocrine synthesis of progesterone, particularly at the level of neurones, is also possible.

Insufficient progesterone secretion in a woman may lead to various disorders, in particular:

premenstrual syndromes, menstrual irregularities through disovulation or anovulation, benign mastopathies, premenopause, menopause.

For the latter indication, progesterone is administered as a complement of an oestrogenic treatment.

Oral administration of progesterone is severely jeopordised because of its high rate of metabolization by the liver.

Yet oral administration has certain obvious advantages compared with other methods of administration. On the one hand it is more practical than vaginal administration, and on the other hand it allows the medication to be taken independently, which is not possible in the case of parenteral administration.

BACKGROUND OF THE INVENTION

The Applicant Company has already proposed a solution to this problem of progesterone degradation in patent application FR 76 36007. The Company has developed a formulation of capsules containing progesterone in an oily suspension which ensures good protection of the active constituent against its degradation by the liver.

The process for manufacturing such capsules has however proven to be both complex and costly to implement, and requires considerable know-how. Attempts have therefore been made to develop efficient and also economically viable alternative formulations.

Accordingly, in European patent no. 0 335 907, the PHARMAGYN Company describes tablets containing micronized progesterone in association with a wax, both in powdery form. It is pointed out in this patent that inclusion of large quantities of wax in the tablets enables to limit the degradation of progesterone by the liver, thereby increasing its bio-availability.

Similarly, in international patent application WO95/05807 the NOVO NORDISK Company describes tablets containing progesterone and a polyethylene glycol, as well as an excipient chosen from the group containing starches, starch-containing components, modified starches, celluloses, modified celluloses, pectins and tragacanth. It is pointed out in this document that the presence of polyethylene glycol and of the excipient in the tablets results in a favourable effect on the bio-availability of orally administered progesterone.

It should be stressed that the tablets described in these two documents contain high percentages of excipients. Tablets made according to the examples given in patent EP 0 335 970 contain 68% excipients, while those in the patent application WO 95/05807 contain about 49% to 62% excipients.

It is known that excipients in tablets play various roles. They are used to increase the stability of the active constituents, to obtain a particular release profile according to the nature of the excipient, but they are mainly used to facilitate compression of the various ingredients in order to obtain a tablet having the desired properties of hardness, disintegration and dissolution.

OBJECTS AND DESCRIPTION THE INVENTION

Figure 1:
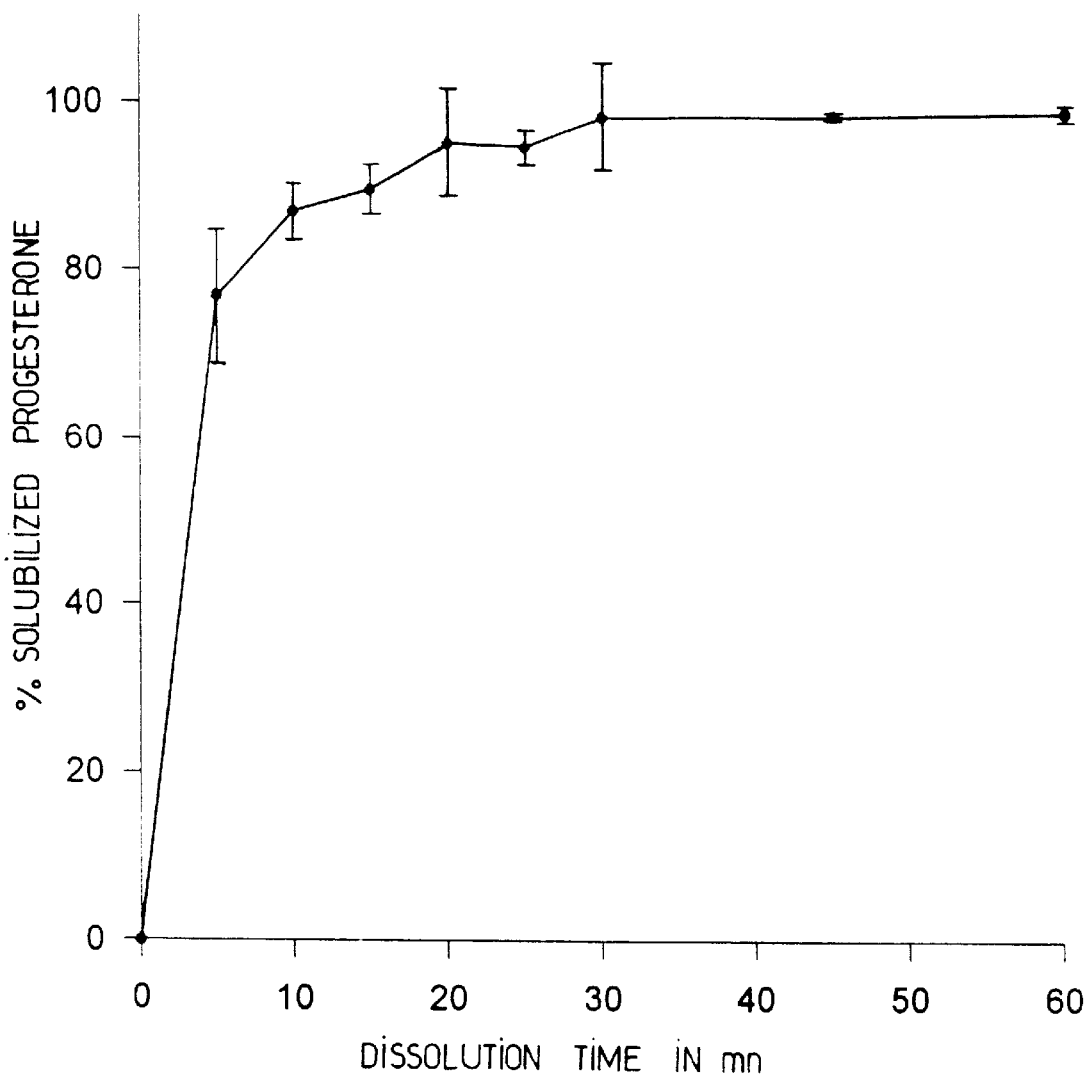
FIG. 1 shows a dissolution profile for a progesterone tablet.

Following much work and research, the Applicant Company managed to develop a new natural progesterone tablet containing only small quantities of excipients.

Quite surprisingly and unexpectedly, although they contain significantly lower quantities of excipients than tablets of the prior art, the tablets developed by the Applicant Company nevertheless show excellent properties of stability, hardness, disintegration and dissolution.

This invention thus concerns a progesterone tablet characterised by the fact that its excipient content is at most 45%, preferably at most 40%, and yet more preferably at most 38%, the percentages being expressed in weight relative to the total dry matter of the tablet.

The tablet according to the invention contains, besides progesterone, diluents, disintegrating agents, lubricants and binding agents.

As examples of diluents, mention may be made of starches, polyols and celluloses. According to the invention the tablet contains preferably pregelatinized maize starch, mannitol and microcrystalline cellulose.

Pregelatinized maize starch is a starch that has been physically modified in order to allow a fluid flow and be directly compressible. It therefore has many advantages in the manufacture of tablets, including improved dissolution and self-lubrication.

Microcrystalline cellulose has good free flowing qualities. Moreover it has good properties as a binding and disintegrating agent, and is thus an ideal excipient for the manufacture of tablets by direct compression.

As examples of disintegrating agents, mention may be made of carboxymethylcelluloses, alginic acid as well as its sodium salt, and starches. The tablet made according to the invention preferably contains reticulated sodium carboxymethylcellulose. This substance was chosen for its qualities as a disintegrating agent as well as for its strong absorbent power.

The preferred lubricant in the context of this invention is magnesium stearate.

The preferred binding agents in the context of this invention include polyvinylpyrollidones, particularly the product marketed under the trademark Polyvidone K30. This product allows quasi immediate release of the active constituent, and is moreover very easy to use.

One of the advantages of the tablet that is the object of the invention is that its disintegration time is less than 15 minutes, preferably less than 10 minutes, and yet more preferably less than 5 minutes.

Another advantage of the tablet according to this invention is that its dissolution profile is such that the released progesterone content released is at least 75% in 15 minutes, preferably in 10 minutes, and yet more preferably in 5 minutes.

The tablet according to this invention has a hardness of between 20 and 120 N, preferably between 30 and 110 N, and yet more preferably between 40 and 100 N.

The invention also concerns a process for the manufacture of progesterone tablets. This process is characterised by the facts that:
a first mixture of progesterone and diluent is prepared,
a wetting suspension is prepared,
the first mixture is then wetted by the wetting suspension,
the product of the wetting is then granulated in order to obtain a granular product,
disintegrating agents and diluents are added to the granular product in order to obtain a second mixture,
a lubricant is added to the second mixture in order to obtain a third mixture,
this third mixture is compressed in order to obtain tablets.

According to a preferential mode of producing the invention, granulation is followed by unclotting, drying and then grading.

MORE DETAILED DESCRIPTION

The invention will be better understood with the help of the non limiting examples described below.

EXAMPLE 1

Progesterone Tablets

The compositions of progesterone tablets according to the invention containing, respectively, 200 and 100 mg of the active constituent are given in Table I, below.

TABLE I

| NAME OF COMPONENT | FUNCTION | QUANTITY mg/tablet | |
|---|---|---|---|
| Progesterone | Active constituent (progestagen) | 200 | 100 |
| Polyvidone K30 | Binding agent | 9.60 | 4.80 |
| Pregelatinized maize starch | Diluent | 92.80 | 46.40 |
| Reticulated sodium carboxymethyl-cellulose | Disintegrating agent | 16.00 | 8.00 |
| Magnesium stearate | Lubricant | 1.60 | 0.80 |

EXAMPLE 2

Preparation of Progesterone Tablets

A batch of tablets containing 100 mg of progesterone per tablet was prepared as described below.
a/ Preparation of the progesterone mixture
30 kg of micronized progesterone (obtained from the DIOSYNTH Company at Oss, Netherlands) and 9.6 kg of pregelatinized maize starch are mixed in the vat of a BONNET type planetary granulator mixer equipped with a Lyre type agitation spindle for ten minutes in order to obtain a homogeneous mixture.

b/ Preparation of the wetting suspension
5.76 l of purified water are put into a stainless steel container. The water is stirred by means of a TURBOTEST RAYNERI mixer equipped with a deflocculation type agitation spindle.
1.44 kg of polyvidone K30 (marketed under the trademark KOLLIDON by the BASF Company) are poured in gradually, and the mixture is then homogenized until the polyvidone is totally dissolved.
c/ Wetting
The wetting solution is trickled onto the mixture of powder contained in the BONNET mixer, the Lyre type spindle being programmed on speed 1, for 30 minutes.
d/ Granulation
The mixture is homogenized for 15 minutes after the wetting is finished in order to obtain a granular powder.
e/ Drying
Drying is carried out in an oven at 40° C. for 6 hours.
f/ Grading
Grading of the granular powder is carried out by means of FREWITT oscillating granulator equipped with a stainless steel sieve with a 1000 µm mesh diameter.
g/ Addition of the disintegrating agents and diluents to the granular product
4.168 kg of pregelatinized starch (AMIDON 1500) and 2.316 kg of reticulated carboxymethylcellulose are added to 39.6 kg of the granular product in the vat of a ROUE RÖHN mixer and mixed for twice five minutes.
0.232 kg of magnesium stearate is added to the mixture thus obtained and mixed for three minutes in order to obtain the final mixture.
h/ Compression of the final mixture
Compression of the final mixture is carried out on a FROGERAIS MR 200 type rotary compressor equipped with stamps. The machine is adjusted in such a way as to obtain a disintegration time of less than about five minutes and a hardness of about 40 N for tablets each weighing 160 mg.

The tablets obtained are packaged in thermally moulded blister strips consisting of a 250 µm thick sheet of PVC sealed with 20 µm thick aluminium foil.

A stability test was carried out on the tablets thus prepared.

They were stocked for 30 days at 45° C. in airtight tinted glass containers.

No alteration in the galenic and analytical parameters was observed at the end of that period, thus showing good stability of the tablets made according to the invention.

EXAMPLE 3

Disintegration Time of Tablets According to the Invention

A tablet prepared according to the method described in example 2 was placed in a beaker containing 600 ml of distilled water brought to a temperature of 37° C. Disintegration time corresponding to a total loss of cohesion was 3 minutes.

EXAMPLE 4

Dissolving Time of Tablets According to the Invention 6 dissolving vats with a capacity of 1000 ml were used. A tablet was placed in each of the vats in a dissolving medium containing 1000 ml of an aqueous solution containing 1% (m/v) sodium laurylsulphate. The solution was then stirred by means of a PARMATEST type PTWS III dissolving apparatus with rotating blades. The blades were immersed in the dissolving medium with a distance of 25 mm±2 mm between the blade and the bottom of the vat. The blades were set to agitate at 75 revolutions per minute.

1 ml of the dissolving medium was sampled every 5 minutes in each vat.

Each sample was dosed by HPLC (=240 ηm) after injection of 20 μl of the solution to be analysed.

The curve given in FIG. 1 shows the dissolution profile obtained. At least 75% of the progesterone is released in 15 minutes of dissolving.

EXAMPLE 5

Bio-Availability of the Progesterone Contained in the Tablets According to the Invention A pharmacokinetic study was carried out on five patients in order to demonstrate the release of progesterone contained in 100 mg tablets having the composition de- scribed in table I above.

Table II below shows concentrations of progesterone released into the blood during the time intervals shown, up to 24 hours after administering the tablet.

Figure 2:
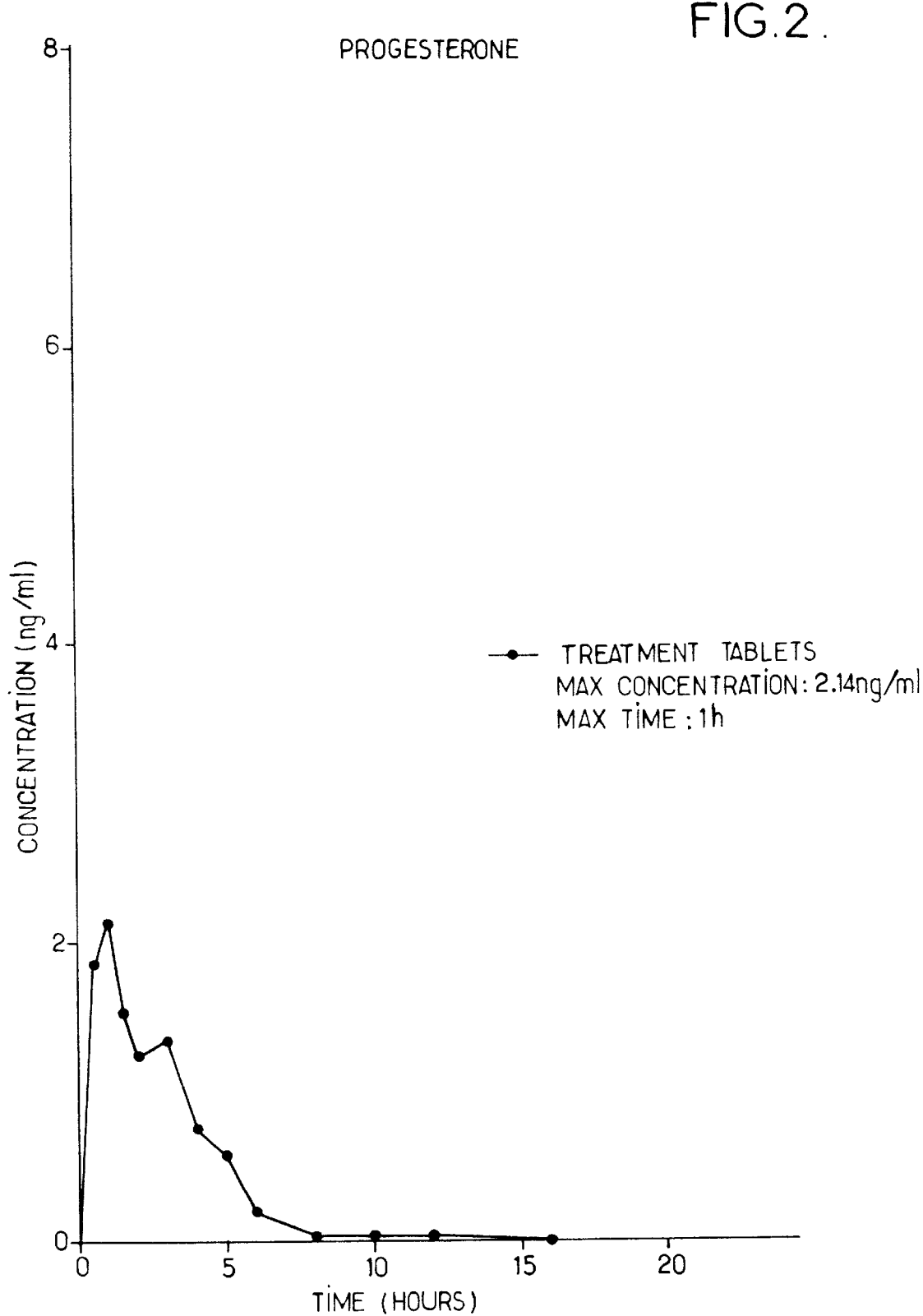
FIG. 2 shows blood concentrations for progesterone.

FIG. 2 shows an average concentration of progesterone released into the blood of the five patients.

These results demonstrate good bio-availability of the progesterone contained in the tablets according to the invention.

TABLE II

TABLETS 100 mg Progesterone Concentration (ng/ml)

| Time | 1 | 2 | 3 | 4 | 5 | Average | Standard deviation |
|---|---|---|---|---|---|---|---|
| 0 | 0,00 | 0,00 | 0,00 | 0,00 | 0,00 | 0,00 | 0,00 |
| 0,5 | 0,00 | 0,49 | 0,34 | 5,23 | 3,24 | 1,86 | 2,29 |
| 1 | 0,18 | 0,86 | 1,86 | 3,68 | 4,13 | 2,14 | 1,72 |
| 1,5 | 0,48 | 0,68 | 1,47 | 2,52 | 2,52 | 1,53 | 0,97 |
| 2 | 0,35 | 1,21 | 1,49 | 1,44 | 1,73 | 1,24 | 0,53 |
| 3 | 0,48 | 1,05 | 1,62 | 0,99 | 2,65 | 1,36 | 0,83 |
| 4 | 0,32 | 0,85 | 0,82 | 0,60 | 1,14 | 0,75 | 0,31 |
| 5 | 0,28 | 0,87 | 0,28 | 0,64 | 0,78 | 0,57 | 0,28 |
| 6 | 0,14 | 0,37 | 0,18 | 0,00 | 0,29 | 0,20 | 0,14 |
| 8 | 0,00 | 0,11 | 0,05 | 0,00 | 0,00 | 0,03 | 0,05 |
| 10 | 0,00 | 0,19 | 0,00 | 0,00 | 0,04 | 0,05 | 0,08 |
| 12 | 0,00 | 0,16 | 0,00 | 0,00 | 0,00 | 0,03 | 0,07 |
| 16 | 0,00 | 0,00 | 0,00 | 0,00 | 0,00 | 0,00 | 0,00 |
| 24 | 0,00 | 0,00 | 0,00 | 0,00 | 0,00 | 0,00 | 0,00 |

What is claimed is:

1. A progesterone tablet containing micronized progesterone, diluents, disintegrating agents, lubricants and binding agents, having:

an excipient content of at most 45%, the percentage being expressed in weight relative to the total dry matter of the tablet, a dissolution profile such that the level of progesterone released is at least 75% in 15 minutes, and a hardness between 20 and 120 N, whereby said tablet shows excellent properties of stability, hardness, disintegration and dissolution.

2. A progesterone tablet according to claim 1, having an excipient content of at most 40%.

3. A progesterone tablet according to claim 2, having an excipient content of at most 38%.

4. A progesterone tablet according to claim 1, having a disintegration time of less than 15 minutes.

5. A progesterone tablet according to claim 4, having a disintegration time of less than 10 minutes.

6. A progesterone tablet according to claim 5, having a disintegration time of less than 5 minutes.

7. A progesterone tablet according to claim 1, having a dissolution profile such that the level of progesterone released is at least 75% in 10 minutes.

8. A progesterone tablet according to claim 7, having a dissolution profile such that the level of progesterone released is at least 75% in 5 minutes.

9. A progesterone tablet according to claim 1, having a hardness between 30 and 110 N.

10. A progesterone tablet according to claim 9, having a hardness between 40 and 100 N.

11. A manufacturing process of a tablet according to claim 1, wherein:

a first mixture of progesterone and diluent is prepared, a wetting suspension is prepared, the first mixture is then wetted by the wetting suspension, the product of the wetting is then granulated in order to obtain a granular product, disintegrating agents and diluents are added to the granular product in order to obtain a second mixture, a lubricant is added to the second mixture in order to obtain a third mixture, this third mixture is compressed in order to obtain tablets.

* * * * *